US009228990B2

(12) United States Patent
Lee et al.

(10) Patent No.: US 9,228,990 B2
(45) Date of Patent: Jan. 5, 2016

(54) SYSTEM FOR PREDICTING PRODUCTION OF FRUIT TREE AND DRIVING METHOD THEREOF

(71) Applicant: Electronics and Telecommunications Research Institute, Daejeon (KR)

(72) Inventors: Sangho Lee, Daegu (KR); Kyuhyung Kim, Daegu (KR); Soo In Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 99 days.

(21) Appl. No.: 14/222,084

(22) Filed: Mar. 21, 2014

(65) Prior Publication Data

US 2014/0314280 A1    Oct. 23, 2014

(30) Foreign Application Priority Data

Apr. 18, 2013  (KR) ........................ 10-2013-0043139

(51) Int. Cl.
*G06K 9/00* (2006.01)
*G01N 33/00* (2006.01)

(52) U.S. Cl.
CPC ........ *G01N 33/0098* (2013.01); *G06K 9/00697* (2013.01)

(58) Field of Classification Search
None
See application file for complete search history.

(56) References Cited

U.S. PATENT DOCUMENTS

| 8,563,805 | B2 * | 10/2013 | Armstrong | ........... C12N 9/0059 435/320.1 |
| 2011/0067147 | A1 * | 3/2011 | Srinivasan | ........... C12N 15/827 800/290 |
| 2013/0325346 | A1 * | 12/2013 | McPeek | ............. G01N 33/0098 702/2 |

FOREIGN PATENT DOCUMENTS

KR    10-1271074 B1    6/2013

OTHER PUBLICATIONS

Aggelopoulou et al., "Yield Prediction in Apple Orchards Based on Image Processing," Precision Agriculture, Aug. 17, 2010.*

* cited by examiner

*Primary Examiner* — Shefali Goradia
(74) *Attorney, Agent, or Firm* — Rabin & Berdo, P.C.

(57) ABSTRACT

Provided is a system for predicting production of a fruit tree, including a plant image obtaining unit collecting images of a fruit tree and confirming identification information about the fruit tree from the collected images, a branch pattern recognizing unit receiving an image of the fruit tree whose identification information is confirmed and extracting fruit bearing branches from among various kinds of branches belonging to the fruit tree, a fruit tree bud recognizing unit receiving an image of each of the extracted fruit bearing branches and extracting information about buds that fruits are actually to be born from among buds belonging to the fruit bearing branch, a meta database storing previous production predicting information about the fruit tree corresponding to the collected images, and a production estimating unit comparing the received bud information and the previous production predicting information to predict production of the fruit tree.

10 Claims, 5 Drawing Sheets

SYSTEM FOR PREDICTING PRODUCTION OF FRUIT TREE AND DRIVING METHOD THEREOF

CROSS-REFERENCE TO RELATED APPLICATIONS

This U.S. non-provisional patent application claims priority under 35 U.S.C. §119 of Korean Patent Application No. 10-2013-0043139, filed on Apr. 18, 2013, the entire contents of which are hereby incorporated by reference.

BACKGROUND OF THE INVENTION

The present invention disclosed herein relates to a system for predicting production of a fruit tree and a driving method thereof, and more particularly, to a system for predicting production of fruit tree by using an imaging device.

A system for predicting production of a fruit tree is used for predicting production of a fruit tree in a next year in advance. Overall price and supply of the fruit tree in the next year can be adjusted on the basis of the production information predicted by the system for predicting production of a fruit tree.

Recently, as the development of electronic technologies, a system for predicting production of a fruit tree by using an imaging device is being developed. The system for predicting production of a fruit tree may predict production of a fruit tree in a next year by collecting image information on the fruit tree from the imaging device and analyzing the collected image information.

In addition, typically, imaging fruit trees is performed at the time when the fruits are actually born. However, it may be difficult to obtain exact fruit tree images due to lots of leaves surrounding the fruits at the time when the fruits are actually born.

SUMMARY OF THE INVENTION

The present invention provides a system for predicting production which predicts production by collecting fruit tree images in a period of dormancy when fruit harvests are completed.

Embodiments of the present invention provide systems for predicting production of a fruit tree, including: a plant image obtaining unit collecting images of a fruit tree and confirming identification information about the fruit tree from the collected images; a branch pattern recognizing unit receiving an image of the fruit tree whose identification information is confirmed and extracting fruit bearing branches from among various kinds of branches belonging to the fruit tree; a fruit tree bud recognizing unit receiving an image of each of the extracted fruit bearing branches and extracting information about buds that fruits are actually to be born from among buds belonging to the fruit bearing branch; a meta database (DB) storing previous production predicting information about the fruit tree corresponding to the collected images; and a production estimating unit receiving the extracted bud information and previous production predicting information about the fruit tree, comparing the received bud information and the previous production predicting information to predict production of the fruit tree.

In other embodiments of the present invention, methods of predicting production of a fruit tree includes: collecting images of a fruit tree; confirming identification information about the fruit tree from the collected images; on the basis of image information about the fruit tree whose identification information is confirmed, extracting patterns of branches belonging to the fruit tree; extracting information about buds that fruits are actually to be born on the basis of the extracted branch patterns; comparing the extracted bud information with previous production prediction information about the fruit tree; and predicting production of the fruit tree on the basis of a compared result, wherein the extracting of the branch patterns comprises analyzing kinds of branches included in the image information about the fruit tree whose identification information is confirmed, extracting information about fruit bearing branches from among the analyzed kinds of branches, and determining ages of the fruit bearing branches from the extracted information about the fruit bearing branches.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Hereinafter, it will be described about an exemplary embodiment of the present invention in conjunction with the accompanying drawings.

Figure 1:
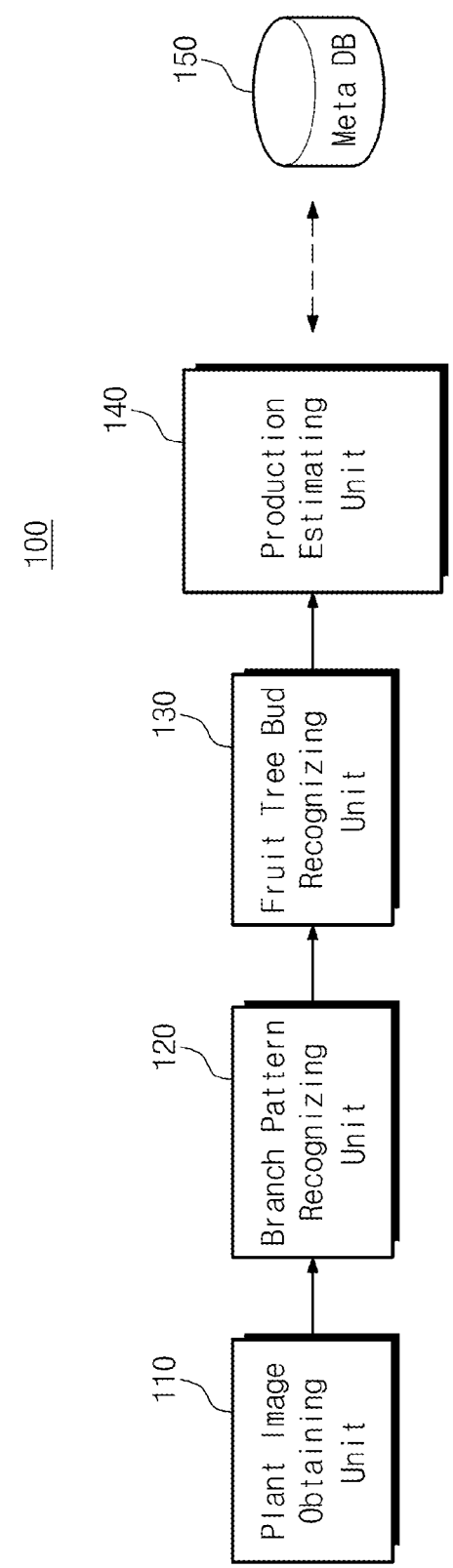
FIG. 1 is a block diagram illustrating a system for predicting production according to an embodiment of the present invention.

FIG. 1 is a block diagram illustrating a system 100 for predicting production. Referring to FIG. 1, the system for predicting production includes a plant image obtaining unit 110, a branch pattern recognizing unit 120, a fruit tree bud recognizing unit 130, a production estimating unit 140, and a meta database (DB) 150. The system 100 for predicting production according to the embodiment of the present invention is described to predict production after a harvest of fruits is completed.

The plant image obtaining unit 110 collects an image of a fruit tree whose production is to be predicted through an imaging device. As the imaging device, an electronic device of a camera type may be used. The plant image obtaining unit 110 collects image information about a fruit tree that is imaged through a camera to confirm identification information about the fruit tree. For example, as the fruit tree identification scheme, a scheme using global positioning system (GPS) information, or a radio frequency (RF) tag scheme may be used.

After confirming the identification information about the fruit tree, the plant image obtaining unit 110 stores the image information about the fruit tree that the identification information is confirmed. The stored fruit tree image information may be used as fruit tree identification information for a next production predicting process. The plant image obtaining unit 110 delivers the image information about the fruit tree whose identification information is confirmed to the branch pattern recognizing unit 120.

The branch pattern recognizing unit 120 receives, from the plant image obtaining unit 110, the image information about the fruit tree whose identification information is confirmed. The branch pattern recognizing unit 110 analyzes kinds and ages of branches on the basis of the received image information about the fruit tree. A kind of branches includes a trunk, a main branch, a secondary scaffold branch, a lateral branch, a bearing mother branch, and a fruit bearing branch.

The branch pattern recognizing unit 120 extracts a branch from the fruit image and determines a kind of the branch. As a scheme for extracting the branch from the fruit image, various image processing schemes may be used. For example, Sobel edge extraction, Prewitt edge extraction, or Roberts edge extraction may be used. The branch pattern recognizing unit 120 extracts an image for a fruit bearing branch among the determined kinds of branches. That is because production may be predicted according to kinds of buds generated in the fruit bearing branch among the kinds of the branches.

In addition, when the kind of branch is analyzed, the branch pattern recognizing unit 120 determines an age of the branch on the basis of the analyzed information. To determine the age of the branch is because a fruit bearing case in the branch differs according to the age. For example, there is a case where a fruit is born in a one year old branch, while there is also a case where a fruit is born in a branch after three year has passed.

The branch pattern recognizing unit 120 may determine an age of a branch by comparing previous image information and current image information. Moreover, when the age of the branch is determined, the branch pattern recognizing unit 120 stores the determined age information as data information. The stored data information may be compared with image information about a branch on which next pattern recognition is performed. The branch pattern recognizing unit 120 delivers the image information about the fruit bearing branch whose age is determined to the fruit tree bud recognizing unit 130.

The fruit tree bud recognizing unit 130 receives the image information about the fruit bearing branch whose age is determined. The fruit tree bud recognizing unit 130 determines kinds of buds on the basis of the received image information about the fruit bearing branch. A kind of bud may include a leaf bud, a flower bud, a mixed bud, an intermediate bud, and a pure flower bud.

The fruit tree bud recognizing unit 130 determines a kind of a bud and confirms whether a flower is germinated on the basis of the determined bud information. On the basis of the number of germinated flowers, fruit production may be predicted. More particularly, the fruit tree bud recognizing unit 130 predicts the number of germinated flowers by extracting information about flower buds and mixed buds among the kinds of buds. Typically, the flower buds and the mixed buds are finally germinated into fruits among the kinds of buds. For example, the fruit tree bud recognizing unit 130 may predict the number of germination of the flower buds and the mixed buds by comparing shapes and sizes of the buds.

Furthermore, the fruit tree bud recognizing unit 130 uses existing data information for confirming germination of a bud. The existing data information means bud information stored in a previous production predicting process. In detail, the fruit tree bud recognizing unit 130 may predict the number of germination of the flower buds and the mixed buds by comparing currently received bud information about the fruit bearing branch with previously stored bud data information. In order to compare the two pieces of data information, various algorithms, such as an image pattern matching scheme, may be used.

Furthermore, the fruit tree bud recognizing unit 130 stores the bud information that the comparison process is completed. The stored information may be used for performing next bud information comparison. The fruit tree recognizing unit 130 delivers the bud information that the number of germinated buds is predicted.

The production estimating unit 140 receives the bud information that the number of germinated buds is predicted from the fruit tree recognizing unit 130. The production estimating unit 140 uses a scheme for comparing currently measured bud information and existing bud information as a scheme for predicting production.

The production estimating unit 140 reads existing production data information from the meta DB 150 and compares the received existing production data with currently predicted bud information. The existing production data information includes a production value that fruits were actually harvested in the next year, in comparison with annual predicted production information.

The production estimating unit 140 may predict production of fruits to be actually born according to the compared result. The production estimating unit 140 may predict what percent of fruits is substantially to be born on the basis of a statistic value of previously performed production prediction. In addition, when an amount of harvested fruits is predicted, the production estimating unit 140 stores the predicted information in the meta DB 150.

The meta DB 150 stores data for the predicted production. The data information stored in the meta DB 150 is used as comparison data in predicting the production.

As described above, the system 100 for predicting production predicts production of fruits in a period of dormancy when fruit harvests are completed. Furthermore, the system 100 for predicting production compares the predicted production of fruits with production of actually harvested fruits. Accordingly, the system 100 for predicting production calculates a difference between the predicted production and the actual production by performing again the prediction of production.

Figure 2:
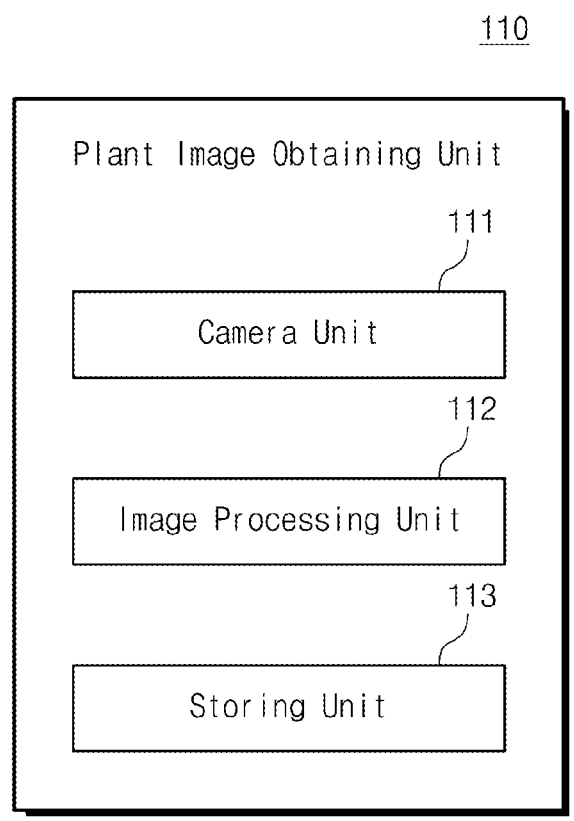
FIG. 2 is a block diagram illustrating the plant image obtaining unit shown in FIG. 1.

FIG. 2 is a block diagram illustrating the plant image obtaining unit shown in FIG. 1. Referring to FIG. 2, the plant image obtaining unit 110 includes a camera unit 111, an image processing unit 112, and a storing unit 113.

The camera unit 111 obtains image information by imaging a fruit tree for which production is to be predicted. The camera unit 111 may be formed of a plurality of cameras and perform imaging in various angles. The camera unit 111 images heights of the fruit tree from the earth and branch shapes of the fruit tree.

More particularly, as the branch grows, germination of a bud may be differed. Typically, a bud of a branch that grows in an opposite direction of the gravity, namely, in a longitudinal direction, is highly possible to germinate into a leaf. On the contrary, a bud of a branch that grows in a traversal direction of the gravity, namely, in a direction parallel to earth surface, is highly possible to germinate into a fruit. Accordingly, the camera unit 111 obtains image information by imaging a shape of a branch in various angles. The image information of fruits imaged from the camera unit 111 is delivered to the image processing unit 112.

The image processing unit 112 receives the image information from the camera unit 111. The image processing unit 112 confirms identification information about the fruit tree on the basis of the received image information. For example, in a case of using GPS information, the image processing unit 112 may find a location of the fruit tree through GPS and confirm the identification information of the fruit tree on the basis of the found information.

The storing unit 113 stores the image information about the fruit tree whose identification information is confirmed. The image information stored in the storing unit 113 includes the identification information about the fruit tree, which is efficiently used when the identical fruit tree is imaged in a next year. For example, when image information about a fruit tree to be imaged is stored in the storing unit 113, the camera unit 111 may efficiently find branches and bud locations of the fruit tree on the basis of the stored image information. Accordingly, the camera unit 111 may image the fruit tree more exactly than imaging a new fruit tree.

Figure 3:
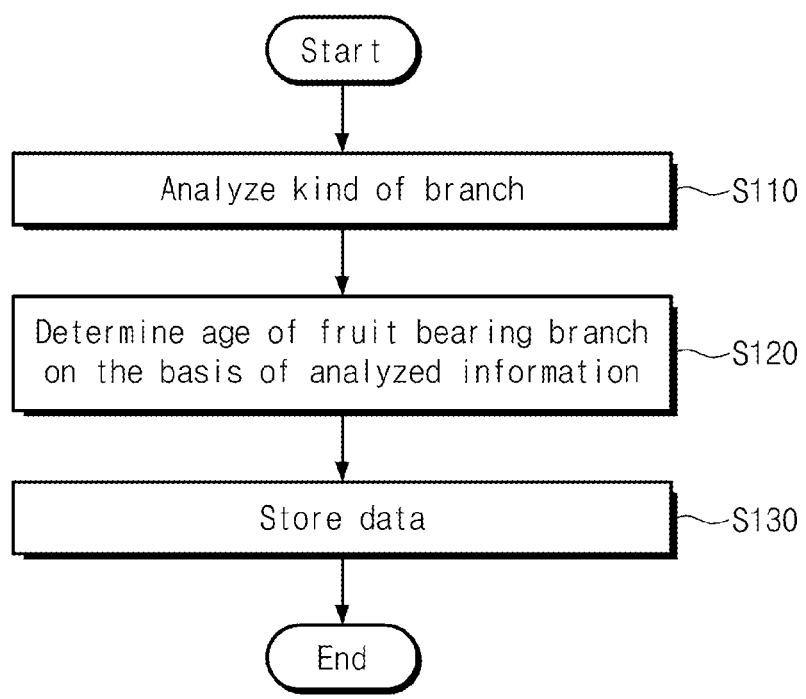
FIG. 3 is a flowchart illustrating an operation of the branch pattern recognizing unit shown in FIG. 1.

FIG. 3 is a flow chart illustrating an operation of the branch pattern recognizing unit shown in FIG. 1. Referring to FIGS. 1 and 3, in operation S110, the branch pattern recognizing unit 120 analyzes kinds of branches on the basis of image information about a fruit tree imaged by the plant image obtaining unit 110. More particularly, the branch pattern recognizing unit 120 finds an image of a fruit bearing branch, which includes bud information, among the kinds of branches.

In operation S120, the branch pattern recognizing unit 120 catches an age of the found fruit bearing branch. The branch pattern recognizing unit 120 may determine a time when flower buds or mixed buds are generated in the fruit bearing branch by referring to the age of the fruit bearing branch. The branch pattern recognizing unit 120 may also confirm the time when flower buds or mixed buds are generated in the fruit bearing branch by comparing existing information with current image information about the fruit bearing branch. Moreover, an existing fruit bearing branch may be identical to the current fruit bearing branch or another fruit bearing branch belonging to the same fruit tree.

In operation S130, the branch pattern recognizing unit 120 stores information about the age of the fruit bearing branch found in operation S120. The age information includes the time when flower buds or mixed buds are generated in the corresponding fruit bearing branch. The stored age information about the fruit bearing branch may be used for a next year age comparison process for the fruit bearing branch.

Figure 4:
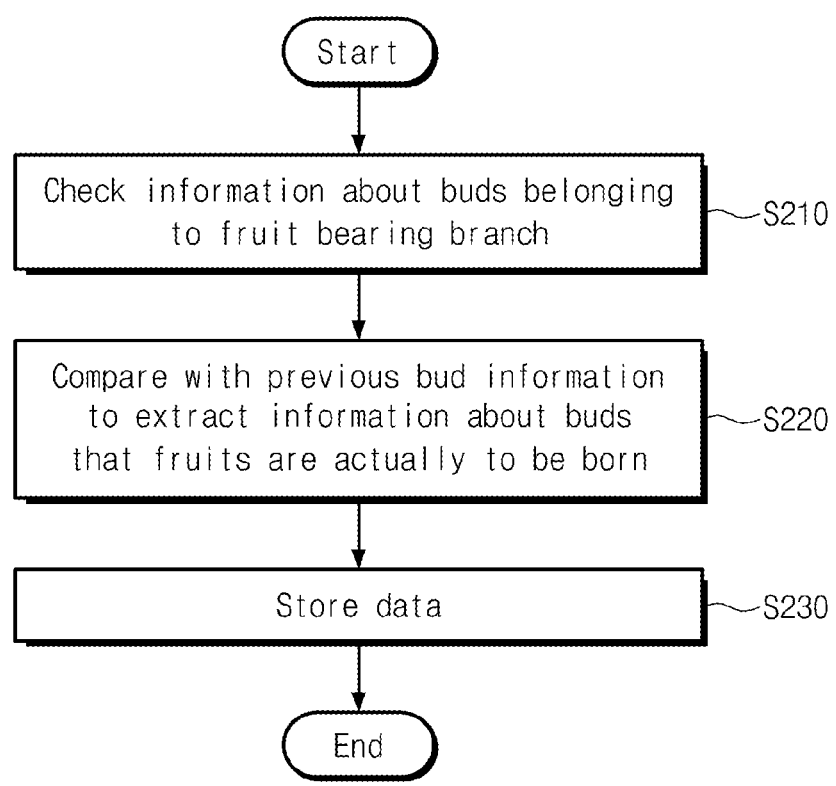
FIG. 4 is a flowchart illustrating an operation of the fruit tree bud recognizing unit shown in FIG. 1.

FIG. 4 is a flow chart illustrating an operation of the fruit tree bud recognition unit shown in FIG. 1. Referring to FIGS. 1 and 4, in operation S210, the fruit tree bud recognizing unit 130 receives information about the found fruit bearing branch from the branch pattern recognizing unit 120 and checks bud information. According to a kind of the bud, it may be determined whether the bud germinates into a leaf or a fruit.

In operation S220, the fruit tree recognizing unit 130 analyzes the checked bud information by comparing information on buds included in the fruit bearing branch and existing bud information. For example, the fruit tree bud recognizing unit 130 may find flower buds or mixed buds in the checked fruit bearing branch by comparing shapes, locations, or sizes of buds. Furthermore, a fruit bearing branch corresponding to the existing bud information may be identical to the checked fruit bearing branch or be another fruit bearing branch belonging to the same fruit tree.

In operation S230, the fruit tree bud recognizing unit 130 stores information about the fruit bearing branch for which finding flower buds or mixed buds is completed. The information about the fruit bearing branch includes shapes, locations, and sizes of the buds. The stored information about the buds of the fruit bearing branch may be used in a next year bud comparison process for the fruit bearing branch.

Figure 5:
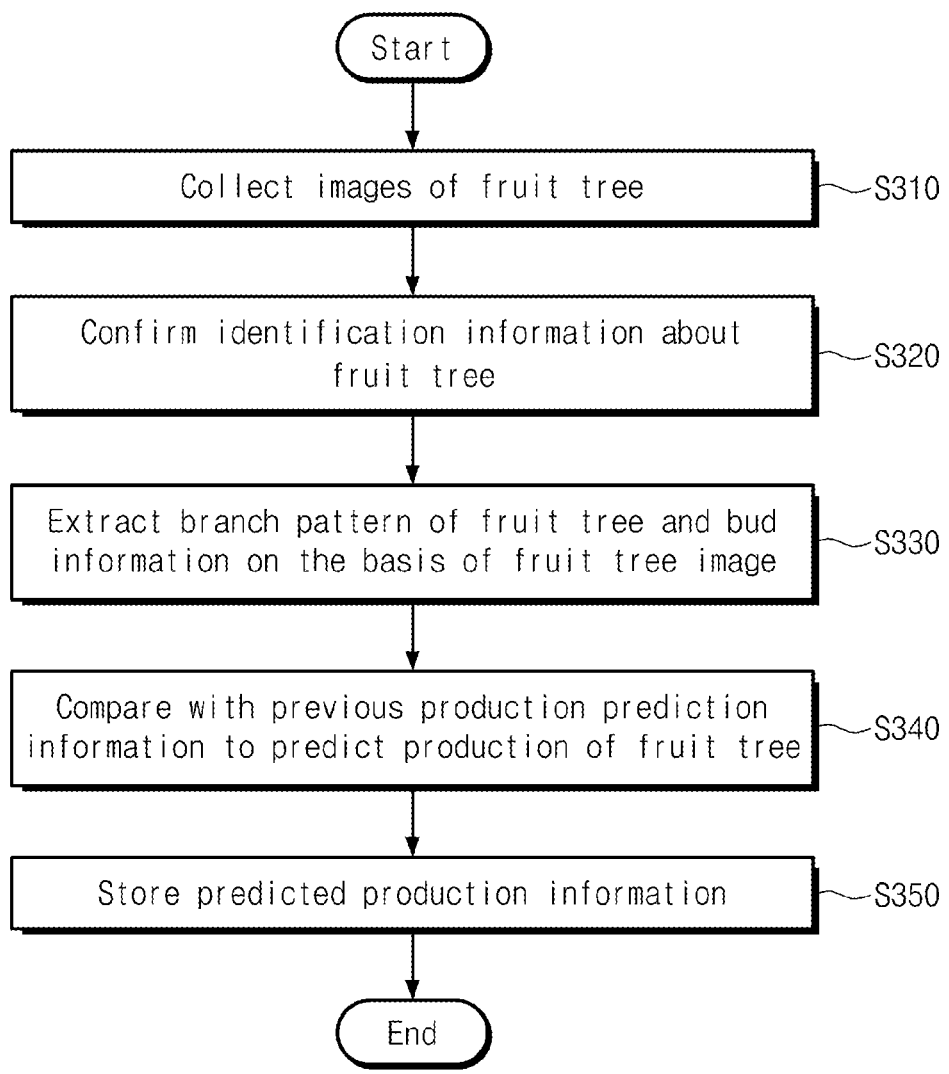
FIG. 5 is a flowchart illustrating an operation of a system for predicting production according to an embodiment of the present invention.

FIG. 5 is a flowchart illustrating a system for predicting production according to an embodiment of the present invention. Referring to FIGS. 1 and 5, in operation S310, the system 100 for predicting production collects images on a fruit tree whose fruit harvest amount is to be predicted.

In operation S320, the system 100 for predicting production confirms identification information about the fruit tee from the collected images. The system 100 for predicting production may compare existing image information and current image information about the fruit tree on the basis of the fruit tree identification information.

In operation S330, the system 100 for predicting production analyzes information about branch patterns and buds of the fruit tree whose identification information is confirmed. The system 100 for predicting production checks the patterns of branches included in the fruit trees and analyzes bud information on the basis of the checked branch patterns. The pattern information about the branches may include kinds and ages of buds. The system 100 for predicting production extracts flower buds or mixed buds among the bud information about the corresponding branch.

In operation 340, the system 100 for predicting production compares the number of flower buds or mixed buds of the fruit tree extracted from operation S330 with the number of buds found from existing production predicting information.

The existing production predicting information may include data that predicted production of fruits and actually harvested amount of the fruits are compared. The system 100 for predicting production may predict production of fruits on the basis of the existing production predicting information.

In operation S350, the system 100 for predicting production stores the predicted production of the fruit tree. Furthermore, the system 100 for predicting production collects data of fruits which are actually born from the fruit tree. The system 100 for predicting production compares prediction information about the fruit tree with information about actually harvested amount and stores the compared information. The stored information may be used in a next production predicting process. The compared data of the prediction information about the fruit tree and the actually harvested amount information may be reflected into annual statistical data and used in an annual production predicting process.

As described above, the system 100 for predicting production performs prediction on production of a fruit tree in a state of dormancy after fruit harvest is completed. The prediction for production in the dormancy state allows patterns of branches and bud information to be exactly figured out, since leaves of the fruit tree are less than those in harvests. In addition, the system 100 for predicting production can determine exact production by predicting production of a fruit tree on the basis of existing production information about the fruit tree.

According to an embodiment of the present invention, a system for predicting production predicts fruit tree production in the next year by using image information about fruit trees that fruit harvests are completed. Accordingly, it can be efficiently used in the agriculture field by exactly predicting productions of fruit trees.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A system for predicting production of a fruit tree, comprising:
    a plant image obtaining unit collecting images of a fruit tree and confirming identification information about the fruit tree from the collected images;
    a branch pattern recognizing unit receiving an image of the fruit tree whose identification information is confirmed and extracting fruit bearing branches from among various kinds of branches belonging to the fruit tree;
    a fruit tree bud recognizing unit receiving an image of each of the extracted fruit bearing branches and extracting information about buds that fruits are actually to be born from among buds belonging to the fruit bearing branch;
    a meta database (DB) storing previous production predicting information about the fruit tree corresponding to the collected images; and
    a production estimating unit receiving the extracted bud information and previous production predicting information about the fruit tree, comparing the received bud information and the previous production predicting information to predict production of the fruit tree.

2. The system according to claim 1, wherein the production prediction for the fruit tree is performed in a dormancy state after a fruit harvest is completed.

3. The system according to claim 1, wherein the plane image obtaining unit comprises:
    a camera unit imaging the fruit tree;
    an image processing unit collecting the images of the imaged fruit tree and confirming the identification information; and
    a storing unit storing the images of fruit tree whose identification information is confirmed,
    wherein the image processing unit confirms the identification information about the imaged fruit tree on the basis of previous fruit tree information stored in the storing unit.

4. The system according to claim 3, wherein the image processing unit confirms the identification information about the fruit tree on the basis of location information of the imaged fruit tree and radio frequency (RF) tag information.

5. The system according to claim 1, wherein the meta DB receives the predicted production information about the fruit tree from the production estimating unit and stores the received information.

6. A method of predicting production of a fruit tree, comprising:
    collecting images of a fruit tree;
    confirming identification information about the fruit tree from the collected images;
    on the basis of image information about the fruit tree whose identification information is confirmed, extracting patterns of branches belonging to the fruit tree;
    extracting information about buds that fruits are actually to be born on the basis of the extracted branch patterns;
    comparing the extracted bud information with previous production prediction information about the fruit tree; and
    predicting production of the fruit tree on the basis of a compared result,
    wherein the extracting of the branch patterns comprises analyzing kinds of branches included in the image information about the fruit tree whose identification information is confirmed, extracting information about fruit bearing branches from among the analyzed kinds of branches, and determining ages of the fruit bearing branches from the extracted information about the fruit bearing branches.

7. The method of claim 6, further comprising storing the predicted production information about the fruit tree.

8. The method of claim 6, further comprising storing the determined ages of the fruit bearing branches.

9. The method of claim 6, wherein the ages of the fruit bearing branches are determined by comparing with previously stored ages of the fruit bearing branches.

10. The method of claim 6, wherein the extracting of the information about buds comprises:
    checking the information about buds belonging to the fruit bearing branches;
    extracting information about buds that fruits are actually to be born from among the checked bud information; and
    storing the extracted bud information.

* * * * *